United States Patent [19]

Saito et al.

[11] Patent Number: 4,657,695
[45] Date of Patent: Apr. 14, 1987

[54] SUBSTITUTED PYRIDAZINES

[75] Inventors: Shinichi Saito; Hiromichi Inoue; Kanetsugu Terashima; Takashi Inukai; Kenji Furukawa, all of Yokohamashi, Japan

[73] Assignee: Chisso Corporation, Osaka, Japan

[21] Appl. No.: 717,097

[22] Filed: Mar. 28, 1985

[30] Foreign Application Priority Data

Apr. 3, 1984 [JP] Japan .................................. 59-66288

[51] Int. Cl.$^4$ .................... C09K 19/34; C07D 237/14; G02F 1/13
[52] U.S. Cl. ........................... 252/299.61; 252/299.65; 252/299.66; 252/299.01; 252/299.1; 350/350 S; 544/239
[58] Field of Search ........... 252/299.61, 299.6, 299.01, 252/299.65, 299.1; 544/224, 239; 350/350 S

[56] References Cited

U.S. PATENT DOCUMENTS

| 3,931,041 | 1/1976 | Saeva et al. | 350/336 |
|---|---|---|---|
| 4,419,262 | 12/1983 | Petrzilka et al. | 252/299.61 |
| 4,452,718 | 6/1984 | Schadt et al. | 252/299.61 |
| 4,460,770 | 7/1984 | Petrzilka et al. | 252/299.61 |
| 4,550,981 | 11/1985 | Petrzilka et al. | 252/299.64 |

FOREIGN PATENT DOCUMENTS

| 110205 | 6/1984 | European Pat. Off. | 252/299.61 |
|---|---|---|---|
| 59-208531 | 11/1984 | Japan | 252/299.61 |

OTHER PUBLICATIONS

Zaschke et al., Z. Chem., 1977, 17(9), 333-334.
Gray et al., MCLC, 1976, vol. 37, pp. 157-188.
Nash et al., MCLC, 1974, vol. 25, pp. 299-321.
Schadt et al., MCLC, 1983, vol. 94, pp. 139-153.
Schadt, MCLC, 1982, vol. 89, pp. 77-92.
Schubert, Wiss. Z. Univ. Halle, 1970, pp. 1-18.
Research Disclosure, 24112, May 1984, pp. 196-197.
Liang, CA 102: 78810h, 1985.
Zaschke et al., CA 88: 6824k, 1978.
Goodby et al., Liq. Cryst. Ord. Fluids, vol. 4, 1984, pp. 1-32, from Proceedings of 1982 ACS Symposium in U.S.A.

Primary Examiner—Teddy S. Gron
Assistant Examiner—J. E. Thomas
Attorney, Agent, or Firm—Wenderoth, Lind & Ponack

[57] ABSTRACT

A liquid crystal compound containing an optically active group, suitable for being used for display mode utilizing ferroelectric liquid crystals, and a composition containing the same are provided, which compound is an optically active pyridazine compound expressed by the general formula

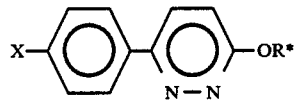

wherein X represents an alkyl group or an alkoxy group each having 1 to 18 carbon atoms and R* represents an optically active group.

6 Claims, No Drawings

SUBSTITUTED PYRIDAZINES

BACKGROUND OF THE INVENTION

1. Field of the Invention

This invention relates to novel liquid crystalline compounds and liquid crystalline mixtures containing the same, and more particularly, it relates to chiral smectic compounds which have a high response rate and are superior as a ferroelectric liquid crystalline material, and also to chiral smectic mixtures containing the same.

2. Description of the Prior Art

Twisted nematic (TN) type display mode has currently been most widely employed as liquid crystal display elements, but it is inferior in response rate as compared with emissive type display elements such as electroluminescence, plasma display, etc., and various attempts for overcoming this drawback have been made. Nevertheless, it seems that its improvement to a large extent has not been fulfilled. Thus, various liquid crystal display equipments based on different principles in place of TN type display elements have been attempted, and as one of them, there is a display mode utilizing ferroelectric liquid crystals (N. A. Clark and S. T. Layerwall, Applied Phys. lett., 36,899 (1980)). This mode utilizes the chiral smectic C phase (hereinafter abbreviated to SC* phase) or chiral smectic H phase (hereinafter abbreviated to SH* phase) of ferroelectric liquid crystals and those are preferred which exhibit these smectic phases at temperatures in the vicinity of room temperature. The present inventors have made various searches for liquid crystal substances containing an optically active group, mainly in order to develop liquid crystal substances suitable for being used for the above display mode, and as a result have attained the present invention.

SUMMARY OF THE INVENTION

The present invention resides in an optically active pyridazine derivative expressed by the general formula

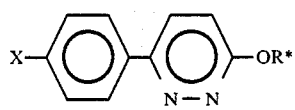

(I)

wherein X represents an alkyl group or an alkoxy group each having 1 to 18 carbon atoms and R* represents an optically active group, and liquid crystal compositions containing the same.

DETAILED DESCRIPTION OF THE PREFERRED EMBODIMENTS

Representative examples of the compounds of the formula (I) of the present invention have phase transition points shown in the following Table 1.

TABLE 1

| Sample No. | In formula (I) X | R* (optically active group) | Phase transition point (°C.) note (1) C | SC* | I | Remark |
| --- | --- | --- | --- | --- | --- | --- |
| 1 | $C_5H_{11}$ | 2-methylbutyl | · 94.0 | — | · | |
| 2 | $C_9H_{19}$ | " | · 77.8 | — | · | Example 1 |
| 3 | $C_{12}H_{25}$ | " | · 78.3 | — | · | |
| 4 | $C_{15}H_{31}$ | " | · 85.3 | — | · | |

TABLE 1-continued

| Sample No. | In formula (I) X | R* (optically active group) | Phase transition point (°C.) note (1) C | SC* | I | Remark |
| --- | --- | --- | --- | --- | --- | --- |
| 5 | $C_8H_{17}O$ | " | · 91.4 | — | · | Example 2 |
| 6 | $C_{10}H_{21}O$ | " | · 87.4 | (· 80.9) | · | |
| 7 | $C_{14}H_{29}O$ | " | · 86.4 | — | · | |
| 8 | $C_5H_{11}$ | 1-methylheptyl | · 54.8 | — | · | |
| 9 | $C_{12}H_{25}$ | " | · 56.3 | — | · | |
| 10 | $C_{10}H_{21}O$ | " | · 87.4 | — | · | |
| 11 | $C_8H_{17}O$ | 1-methylbutyl | · 84.8 | — | · | |

Note (1): C represents a crystalline phase and I, an isotropic liquid phase; the numeral figures on the right side of the symbol · in the column of the respective phases represent transition points from a phase to that on the right side thereof and the symbol — indicates that the phase above it is not observed; and the symbol ( ) indicates that the temperature is a monotropic transition point.

In Table 1, the case where smectic phase is directly observed with a single compound is only one (sample No. 6), but when a plurality of compounds are mixed together, the resulting mixture exhibits a liquid-crystalline phase (see Table 2 described later). In view of this fact, even in the form of a single compound, it can be said that those compounds of the formula (I) wherein X represents an alkyl group substantially have smectic A phase (SA phase) at temperatures below their melting points, while those of the formula (I) wherein X represents an alkoxy group substantially have SC* phase at temperatures below their melting points (see Table 2). Namely, by mixing together compounds of the formula (I) having different alkyl groups as X and thereby lowering their melting points, SA phase tends to be observed, while by mixing together compounds of the formula (I) having different alkoxy groups as X and thereby lowering their melting points, SC* phase tends to be observed. Further, by mixing those compounds having an alkyl group as X with those having an alkoxy group as X, there can be obtained a liquid crystal composition exhibiting SA phase alone, a liquid crystal composition exhibiting SC* phase alone, a liquid crystal composition having SA phase at temperatures above those of SC* phase, etc., depending on their mutual proportion (see Examples 3–8).

Next, the values of the spontaneous polarization of the compounds of the present invention will be described.

Compounds of the formula (I) wherein R* represents 2-methylbutyl group (sample Nos. 1–7) have an extrapolation value of spontaneous polarization of about 4 nanocoulomb/cm². Compounds of the formula (I) wherein R* represents 1-methylheptyl group have an extrapolation value of spontaneous polarization exceeding about 100 nanocoulomb/cm²; for example, the compound of sample No. 10 has about 112 nanocoulomb/cm² in terms of an extrapolation value Ps from the value of spontaneous polarization measured in a Sc* mixture thereof with S-4'-(2-methyl-butoxycarbonyl)-4-biphenylyl p-heptyloxybenzoate. Further, the S form of the compound of sample No. 10 has a positive value of spontaneous polarization, while the R form thereof has a negative value of spontaneous polarization.

When chiral smectic liquid crystal compositions are formed using the compounds of the formula (I), it is possible to form them from a plurality of compounds of the formula (I), alone, and it is also possible to prepare liquid crystalline compositions exhibiting SC* phase, by mixing compounds of the formula (I) with other smectic liquid crystals.

When the light switching effect of the SC* phase is applied to display elements, the resulting display elements have the following three superior specific features:

The first specific feature is that the elements reply at a very high rate and the response times are 1/100 or less of those of display elements according to the usual TN display mode.

The second specific feature is that the elements have a memory effect; hence multiplex drive is easy in combination of this effect with the above-mentioned high rate response properties.

The third specific feature is that gray scale in TN display mode is attained by controlling the impressed voltage applied to display elements, but this is accompanied with difficult problems of the temperature dependency of threshold voltage value and the voltage dependency of response rate. However, in the case where the light switching effect of SC* phase is applied to the display elements, it is possible to easily attain the gray scale by controlling the switching time of polarity; hence the display elements are very suitable for graphic display.

As for the display modes, the following two may be considered:

one mode is of birefringence type using two pieces of polarizers and another is of guest-host type using dichroic dyestuffs. Since SC* phase has a spontaneous polarization, molecules reverse arond the helical axis thereof as a revolving axis by reversing the polarity of impressed voltage. A liquid crystal composition having SC* phase is filled into a liquid crystal display cell subjected to an aligning treatment so that liquid crystal molecules can align in parallel relation to the surface of electrodes, followed by placing the liquid crystal cell between two pieces of polarizers arranged so that the director of the liquid crystal molecules can be in parallel to the polarization plane on another side, impressing a voltage and reversing the polarity to be thereby able to obtain a bright field and a dark field (determined by the opposed angles of polarizers). On the other hand, in the case where display elements are operated in guest-host mode, it is possible to obtain bright field and colored field (determined by the arrangement of polarization sheets) by reversing the polarity of impressed voltage.

In general, it is difficult to align liquid crystal molecules in smectic state in parallel to the wall surface of glass; hence liquid crystal molecules have been aligned by cooling them very slowly (e.g. 1°-2° C./hr) initially starting from their isotropic liquid, in a magnetic field of several tens Kilogauss or more, but in the case of liquid crystal substances having cholesteric phase, the substances are cooled at a cooling rate of 1° C./min. under impression of a direct current voltage of 50 to 100 V in place of magnetic field, whereby it is possible to easily obtain a monodomain state where liquid crystal molecules are uniformly aligned.

As to the racemic form compounds corresponding to the optically active form compounds of the formula (I), when 2-methyl-1-butanol of racemic form is used as raw material in place of S(−)-2-methyl-1-butanol in the preparation of an optically acitve form compound mentioned below, then the racemic form compound is similarly prepared, and exhibits almost the same phase transition point as that of (I). Racemic form compounds exhibit a SC phase in place of a SC* phase, and when they are added to the optically active compounds of the formula (I), they are usable for controlling the chiral smectic pitch thereof.

Compounds of the formula (I) also have an optically active carbon atom; hence when they are added to nematic liquid crystals, they have a performance of having a twisted structure induced in the mixtures. Nematic liquid crystals having a twisted structure, i.e. chiral nematic liquid crystals, do not form the so-called reverse domain of TN type display elements; hence it is possible to use the compounds of the formula (I) as an agent for preventing the reverse domain.

Next, preparation of the compounds of the formula (I) will be described. It is possible to prepare the compounds most suitably according to the following steps:

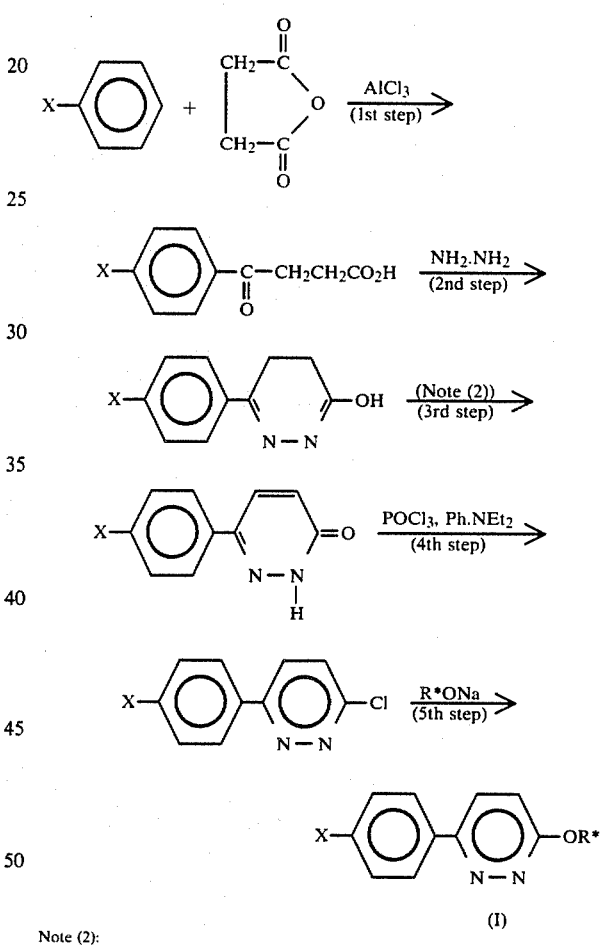

Note (2):
In the case of X = alkyl group, the compound is heated with bromine in acetic acid.
In the case of X = alkoxy group, the compound is heated with selenium disulfide in dioxane.

The liquid crystal compounds and the liquid crystal composition of the present invention will be described in more detail by way of Examples.

EXAMPLE 1

Preparation of S-3-(2-methylbutoxy)-6-(4'-nonylphenyl)-pyridazine (a compound of the formula (I) wherein X=C$_9$H$_{19}$ and R*=S-2-methylbutyl, Sample No. 2)

First step n-Nonylbenzene (186 g, 0.913 mol), succinic anhydride (92.4 g, 0.924 mol) and carbon disulfide (1 l) were agitated at room temperature, followed by adding anhydrous aluminum chloride (266 g, 2 mols), agitating the mixture for 15 minutes, further agitating on a water bath at 50° C. for 3 hours, allowing to cool down to room temperature, adding to ice (about 1.5 Kg), distilling off carbon disulfide, collecting solids, adding toluene (1 l), distilling off water on heating, filtering while hot, and allowing the resulting solids to stand overnight in a cold place to obtain colorless crystals (195 g, mp 103° C.). This product is β-(p-nonylbenzoyl)-propionic acid (yield 70.2%).

Second step

A mixture of β-(p-nonylbenzoyl)-propionic acid (191 g, 0.629 mol) obtained in the first step with water (500 ml) was heated to 60° C. with stirring, followed by dropwise adding 80% hydrazine hydrate (106 g, 2.66 mols), further agitating the mixture at 80° C. for 2 hours, collecting deposited crystals and recrystallizing from ethanol (1.2 l) to obtain yellow crystals (172.6 g). This product is 6-(4'-nonylphenyl)-4,5-dihydro-3(2H)pyridazinone having a m.p. (C-SA point) of 94.4° C. and a SA-I point of 115.7° C. Yield: 91.6%.

Third step 6-(4'-Nonylphenyl)-4,5-dihydro-3(2H)pyridazinone (129.7 g, 0.432 mol) and acetic acid (240 ml) were agitated at 80° C., followed by dropwise adding a mixed solution of bromine (74.5 g, 0.466 mol) and acetic acid (80 ml), ice-cooling the resulting mixture after disappearance of bromine color, collecting solids and recrystallizing from ethanol (0.8 l) to obtain colorless crystals (116.6 g, yield 90.5%, mp 153.6° C.). This product is 6-(4'-nonylphenyl)-3(2H)pyridazinone.

Fourth step 6-(4'-Nonylphenyl)-3(2H)pyridazinone (28.3 g, 0.095 mol) obtained in the third step, phosphorus oxychloride (95.5 g, 0.623 mol) and N,N-dimethylaniline (7.5 g, 0.050 mol) were agitated at 80° C. for one hour, followed by further heating the mixture under reflux for 3 hours, lowering the temperature to room temperature, distilling off excess phosphorus oxychloride under reduced pressure, mixing the residue with ice (300 g), collecting deposited solids and recrystallizing from ethanol (500 ml) to obtain blue-white crystals (22.1 g, yield 73.5%) having a m.p. of 112.6° C. (monotropic SA-I point: 108.4° C.). This product is 3-chloro-6-(4'-nonylphenyl)pyridazine.

Fifth step

Metallic sodium (1.33 g, 0.057 atom equivalent) was added to a mixture of S(−)-2-methylbutanol (12.5 g, 0.142 mol) with anhydrous benzene (40 ml) to prepare a sodium alkoxide, to which 3-chloro-6-(4'-nonylphenyl)-pyridazine (16.2 g, 0.0512 mol) obtained in the fourth step was added at room temperature, followed by heating the mixture under reflux for 3 hours, adding water and toluene, water-washing the toluene layer, distilling off toluene and recrystallizing from ethanol (300 ml) to obtain colorless crystals (11.7 g, mp 77.8° C.). This product is S-3-(2-methylbutoxy)-6-(4'-nonylphenyl)-pyridazine as the objective final product.

EXAMPLE 2

Preparation of
S-3-(2-methylbutoxy)-6-(4'-octyloxyphenyl)-pyridazine
(a compound of the formula (I) wherein X=C$_8$H$_{17}$O
and R*=S-2-methylbutyl, Sample No. 5)

First step n-Octyloxybenzene (301 g, 1.46 mol), succinic anhydride (146.8 g, 1.468 mol) and carbon disulfide (1.3 l) were agitated at room temperature, followed by portion-wise feeding anhydrous aluminum chloride (392 g, 2.94 mol), further agitating the mixture at 50° C. for 4 hours after the reaction became quiet, cooling the mixture down to room temperature, adding it to ice (2 Kg), distilling off carbon disulfide, collecting solids, adding toluene (1 l), distilling off water on heating, filtering while hot, and distilling off toluene under reduced pressure to obtain oily β-(p-octyloxybenzoyl)-propionic acid (238 g, yield 53%).

Second step

β-(p-octyloxybenzoyl)-propionic acid (237 g, 0.777 mol) obtained in the first step and water (800 ml) were heated to 60° C. with stirring, followed by dropwise adding 80% hydrazine hydrate (128 g, 3.2 mols), further agitating the mixture at 80° C. for 3 hours, collecting deposited crystals and recrystallizing from ethanol (1.5 l) to obtain yellow crystals (74 g). This product is 6-(4'-octyloxyphenyl)-4,5-dihydro-3(2H)pyridazinone having a m.p. (C-SA point) of 99.5° C. and a SA-I point of 116.5° C. Yield: 31.6%.

Third step 6-(4'-Octyloxyphenyl)-4,5-dihydro-3(2H)pyridazinone (73.9 g, 0.245 mol) obtained in the second step, 1,4-dioxane (150 ml) and water (12 ml) were agitated at room temperature, followed by further adding selenium dioxide (20.6 g, 0.186 mol), heating the mixture under reflux for 4 hours, distilling off the solvent, filtering residue while hot from ethanol (300 ml), and recrystallizing to obtain colorless crystals (46.8 g, mp 150° C.). This product is 6-(4'-octyloxyphenyl)-3(2H)-pyridazinone. Yield: 64%.

Fourth step 6-(4'-Octyloxyphenyl)-3(2H)-pyridazinone (30.1 g) obtained in the third step was reacted with phosphorus oxychloride and N,N'-dimethylaniline as in the case of the fourth step of Example 1, and the resulting raw 3-chloro-6-(4'-octyloxyphenyl)-pyridazine was recrystallized from ethyl acetate to obtain as a purified product, colorless crystals (20.7 g, yield 64.8%) having a m.p. (C-SA point) of 126° C. and a SA-I point of 150° C.

Fifth step

3-Chloro-6-(4'-octyloxyphenyl)-pyridazine (12.3 g) obtained in the fourth step was reacted with a sodium alkoxide as in the case of the fifth step of Example 1, and the resulting raw S-3-(2-methylbutoxy)-6-(4'-octyloxyphenyl)-pyridazine was recrystallized from ethanol to obtain as a purified product, colorless crystals (m.p. 91.4° C., 11.2 g). Yield: 78.4%.

Other compounds of the formula (I) indicated in Table 1 (sample Nos. 3–11) also were obtained as in Examples 1 and 2.

EXAMPLES 3–8 (COMPOSITION)

Liquid crystal compositions consisting only of compounds of the formula (I) were prepared and their phase transition points were measured. The results are shown in Table 2. The respective proportions of compounds of the formula (I) as components are all in equal amounts.

TABLE 2

| Example | Composition (numeral indicates Sample No.) | Phase transition point (°C.) | | | |
|---|---|---|---|---|---|
| | | C | SC* | SA | I |
| 3 | 2, 5, 6 | · 81.7 | · 82.7 | — | · |
| 4 | 5, 6, 7 | · 72.4 | · 77.9 | — | · |
| 5 | 4, 6 | · 63 | — | · 64.7 | · |

TABLE 2-continued

| Example | Composition (numeral indicates Sample No.) | Phase transition point (°C.) | | | |
|---|---|---|---|---|---|
| | | C | SC* | SA | I |
| 6 | 2, 3, 6 | · 60 | — | · 60.7 | · |
| 7 | 2, 5, 6, 7 | · 62.2 | · 71.6 | — | · |
| 8 | 2, 3, 4, 5, 6, 7 | · 54.2 | · 55.4 | · 63.7 | · |

EXAMPLES 9-11 (COMPOSITION AND USE EXAMPLE)

p-Hexyloxyphenyl S-4-(2-methylbutyl)-4'-biphenylcarboxylate is a known liquid crystal compound having a C-SC* point of 58° C., a SC*-Ch point of 80° C. and a Ch-I point of 155° C. (hereinafter abbreviated to compound (II)). Liquid crystal compositions were prepared from this compound and compounds (I) of the present invention, and their phase transition points were measured. The results are shown in Table 3.

TABLE 3

| Example | Composition (parts by weight) | | | Phase transition point (°C.) | | | |
|---|---|---|---|---|---|---|---|
| | Compound (II) | Sample No. 2 | Sample No. 6 | C | SC* | Ch | I |
| 9 | 50 | 25 | 25 | · 48 | · 77 | · 89 | · |
| 10 | 30 | 35 | 35 | · 52 | · 75 | — | · |
| 11 | 10 | 45 | 45 | · 57 | · 68 | — | · |

The liquid crystal composition of Example 10 in the above Table was filled in a cell provided with transparent electrodes coated with PVA (polyvinyl alcohol) as an agent for aligning treatment and subjected to parallel aligning treatment by rubbing the surface, and the cell was gradually cooled from the isotropic liquid region till SC* phase was attained, under impression of a direct current voltage of 50 V. This liquid crystal cell was placed between two sheets of polarizers arranged in a crossed Nicol state, and a low frequency alternating current of 0.5 Hz and 15 V was impressed. As a result, a clear switching operation was observed; and a liquid crystal display element having a very good contrast and a high response rate (2 m sec) was obtained.

In addition, the value of spontaneous polarization (Ps) was 2.5 nC/cm$^3$.

To the above mixture was added an anthraquinone dyestuff (D-16, a product made by BDH Company) in an amount of 3% by weight to prepare a liquid crystal composition of the so-called guest-host type, which was filled in the same liquid crystal cell as above. One sheet of polarizer was arranged so that its polarization plane might be perpendicular to the molecular axis and a low frequency alternating current of 0.5 Hz and 15 V was impressed. As a result, a clear switching operation was observed and a color liquid crystal display element having a very good contrast and a high response rate (2 m sec) was obtained.

EXAMPLE 12 (USE EXAMPLE)

A nematic liquid crystal composition consisting of
4-ethyl-4'-cyanobiphenyl: 20% by weight,
4-pentyl-4'-cyanobiphenyl: 40% by weight,
4-octyloxy-4'-cyanobiphenyl: 25% by weight, and
4-pentyl-4'-cyanoterphenyl: 15% by weight, was filled in a cell (electrode distance: 10 μm) comprising transparent electrodes coated with PVA as an agent for aligning treatment and subjected to parallel aligning treatment by rubbing the surface to prepare a TN type cell, which was then observed by a polarization microscope. As a result, formation of a reverse domain was observed.

To the above nematic liquid crystal composition was added a compound of sample No. 4 or that of sample No. 10 in an amount of 1% by weight, and using these compositions, TN cells were prepared as above and observed. As a result, the above reverse domain was dissolved and a uniform nematic phase was observed.

What we claim is:

1. An optically active pyridazine compound of the formula

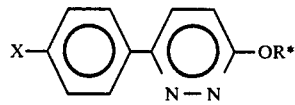

wherein X represents an alkyl group having 5 to 15 carbon atoms or an alkoxy group having 8 to 14 carbon atoms and R* represents an optically active alkyl group of up to 8 carbon atoms and having one methyl group as its side chain.

2. An optically active pyridazine derivative according to claim 1 wherein R* represents 1-methylbutyl group.

3. An optically active pyridazine derivative according to claim 1 wherein said R* represents 2-methylbutyl group.

4. An optically active pyridazine derivative according to claim 1 wherein R* represents 1-methylheptyl group.

5. A chiral smectic liquid crystal composition having at least two components at least one of which is selected from the compounds set forth in claim 1.

6. A light switching element containing a chiral smectic liquid crystal composition according to claim 5.

* * * * *